United States Patent [19]
Tang et al.

[11] Patent Number: 5,512,675
[45] Date of Patent: Apr. 30, 1996

[54] METHODS FOR PREPARING PORPHYRIN-LIKE COMPOUNDS

[75] Inventors: Hang Tang; Lily Xie, both of Vancouver, Canada; Tilak Wijesekera, Glen Mills, Pa.; David Dolphin, Vancouver, Canada

[73] Assignee: The University of British Columbia, Vancouver, Canada

[21] Appl. No.: 77,789

[22] Filed: Jun. 15, 1993

Related U.S. Application Data

[63] Continuation-in-part of Ser. No. 968,966, Oct. 30, 1992.
[51] Int. Cl.$^6$ .................................................. C07D 487/22
[52] U.S. Cl. .......................................... 540/472; 540/145
[58] Field of Search .................................. 540/145, 472

[56] References Cited

U.S. PATENT DOCUMENTS

| | | | |
|---|---|---|---|
| 4,798,891 | 1/1989 | Franck et al. | 540/145 |
| 5,051,415 | 9/1991 | Morgan et al. | 540/145 |
| 5,124,449 | 6/1992 | Franck et al. | 540/145 |
| 5,162,509 | 11/1992 | Sessler et al. | |

OTHER PUBLICATIONS

Barnett et al., "Pyrrole chemistry. XII. Synthetic Approaches to Cyanopyrroles", *Can J. Chem.*, 58, 409–411 (1979).

Demopoulos et al., "Pyrrole Chemistry. XXVI. A Synthesis of Porphobilinogen from Pyrrole", *Can. J. Chem.*, 61, 2415–76 (1983).

Loader et al., "Pyrrole Chemistry. XXIII. The Cyanation of Substituted Pyrroles with Chlorosulfonyl Isocyanate (CSI). New Synthesie of Pyrrole-3-carbonitriles", *Can. J. Chem.*, 59, 2673–76 (1981).

Dhar et al., "Recent Advances in the Chemistry of Chlorosulfonyl Isocyanate", *Synthesis*, 437–49 (1986).

Floyd et al., "Direct Cyanation of the Furan Nucleus by Chlorosulphonyl Isocyanate", *Tetrahedron*, 39, 3881–85 (1983): and Vorbruggen, "Reaktive Isocyanate I. Die Direkte Einfuehrung von Nitril–Gruppen in Ungesattigte System. Eine Einfache Umwandlung von Carbonsauren in Ihre Nitrile", *Tetrahedron Letters*, 13, 1631–34 (1968).

"Photoradiation Therapy—Clinical and Drug Advances" and Intra-abdominal Applications of Hematoporphyrin Photoradiation Therapy, *Porphyrin Photosensitization*, 3–13, 15–21 (Kessel et al., eds 1983).

Broadhurst et al., "The Synthesis of 22 π–Electron Macrocycles: Sapphyrins and Related Compounds", *J. Amer. Chem. Soc. (1972) 1:2111–2116.*

Bauer et al., "Sapphyrins: Novel Aromatic Pentapyrrolic Macrocycles", *J. Amer. Chem. Soc.* (1983) 105:6429–6436.

Day et al., "Large Metal Ion–Centered Template Reactions. A Uranyl Complex of Cyclopentakis(2–iminoisoindoline)", *J. Amer. Chem. Soc.* (1975) 97:4519–4527.

Marks et al., "Large Metal Ion–Centered Template Reactions. Chemical and Spectral Studies of the 'Superphthalocyanine' Dioxocyclopentakis(1–iminoisoin–dilinato)uranium(VI) and Its Derivatives", *J. Amer. Chem. Soc. (1978) 100:1695–1705.*

Gossauer, A., "Syntheses of Some Unusual Polypyrrole Macrocycles", *Bull. Soc. Chim. Belg.* (1983) 92(9):793–795.

Sessler et al., "Rubyrin: A New Hexapyrrolic Expanded Porphyrin", *Agnew, Chem. Int. Ed. Engl.* (1991) 30(8):977–980.

Berger et al., "The Synthesis Of A 22π–Electron Tetrapyrrolic Macrocycle, [1,3,1,3] Platyrin", *Tetra. Lett. (1978) 44:4225–4228.*

LeGoff et al., "Perchloro–7H–cycloprop[a]acenaphthylene and the Percholorophenalenyl System", *J. Org. Chem.* (1987) 52:711–712.

Franck et al., "Chemical principles in the design of improved porphyrin photosensitizers", *Proc. SPIE Int. Soc. Opt. Eng.* (1988) 997:107–112.

Beckmann et al., "[22]Coproporphyrin II for Photodynamic Therapy", *Agnew. Chem. Int. Ed. Engl.* (1990) 29:1395–1397.

Gosmann et al., "Systhesis of a Fourfold Enlarged Porphyrin with an Extremely Large, Diamagnetic Ring–Current Effect", *Agnew Chem. Int. Ed. Engl.* (1986) 25:1100–1101.

Knübel et al., "Biomimetic Synthesis of an Octavinylogous Porphyrin with an Aromatic [34]Annulene System", *Agnew. Chem. Int. Ed. Engl.* (1988) 27:1170–1172.

(List continued on next page.)

Primary Examiner—Mukund J. Shah
Assistant Examiner—Pavanaram K. Sripada
Attorney, Agent, or Firm—Morrison & Foerster

[57] ABSTRACT

A method for synthesizing a porphocyanine having the formula:

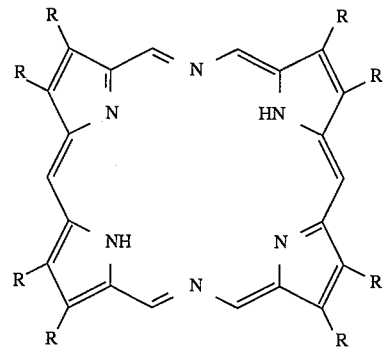

where each R is ethyl, comprises either:
(1) treating 3,3'-4,4'-tetraethyl-5,5'-bisaminomethyl-2,2'-dipyrromethane with a 10-fold excess of DDQ or
(2) treating 3,3'-4,4'-tetraethyl-5,5'-diformyl 2,2'-dipyrromethane with ammonia, followed by column chromatography purification and evaporating to dryness the eluant containing the purified product.

2 Claims, 10 Drawing Sheets

OTHER PUBLICATIONS

Jux et al., "Acetylene–Cumulene Porphyrinoids", *Agnew Chem. Int. Ed. Engl.* (1990) 29:1385–1387.

Vogel et al., "Porphyrin Homologues: [22]Porphyrin(2.2.2.2), a 'Stretched Porphycene'", *Agnew Chem. Int. Ed. Engl.* (1990) 29:1387–1390.

Sessler et al., "Synthesis and Crystal Structure of a Novel Tripyrrane–Containing Porphyrinogen–like Macrocycle", *J. Org. Chem.* (1987) 52:4394–4397.

Sessler et al., "An 'Expanded Porphyrin': The Synthesis and Structure of a New Aromatic Pentadentate Ligand", *J. Am. Chem. Soc.* (1988) 110:5586–5588.

Ssssler et al., "Synthesis and X–ray Characterization of a Uranyl(VI) Schiff Base Complex Derived from a 2:2 Condensation Product of 3,4–Diethylpyrrole–2,5–dicarbaldehyde and 1,2–Diamino–4,5–dimethyoxybenzene", *Inorg. Chem.* (1992) 31(4):529–531.

Gregorie, Jr., et al., "Hematoporphyrin–Derivative Fluorescense in Malignant Neoplasms", *Ann. Surg.* (1968) 167:820–828.

Diamond et al., "Photodynamic Therapy of Malignant Tumours", *Lancet* (1972) 2:1175–1177.

Dougherty et al., "Photoradiation Therapy for the Treatment of Malignant Tumors", *Cancer Res.* (1978) 38:2628≧2635.

Regan et al., eds., *The Science of Photomedicine* (1992) Plenum Press, New York. The title page and table of contents is enclosed herewith.

Dougherty et al., "Photosensitizers", *Cancer: Principles and Practice of Oncology*, J. B. Lippincott Company, Philadelphia (1982) DeVita, Jr. et al. eds., Section 4, pp. 1836–1844.

Maiya et al., "In Vitro Photodynamic Activity of Diprotonated Sapphyrin: A 22–π–Electron Pentapyrrolic Porphyrin–like Macrocycle", *J. Phys. Chem.* (1990) 94:3597–3601.

Sessler et al., "Tripyrroledimethine–derived ('texaphyrin'–type) macrocycles: Potential photosensitizers which absorb in the far–red spectral region", *SPIE* (1991) 1426:318–329.

Lauffer, R. B., "Paramagnetic Metal Complexes as Water Proton Relaxation Agents for NMR Imaging: Theory and Design", *Chem. Rev.* (1987) 87:901–927.

Kornguth et al., "Magnetic resonance imaging of gadolinium–labeled monoclonal antibody polymers directed at human T lymphocytes implanted in canine brain", *J. Neurosurg.* (1987) 66:898–906.

Koenig et al., "Magnetic Field Dependence (NMRD) profile of 1/T1 of Rabbit Kidney Medulla and Urine After Intravenous Injection of Gd(DTPA)", *Invest Radiol.* (1986) 21:697–704.

Cacheris et al., "Thermodynamic Study of Lanthanide Complexes of 1,4,7–Triazacyclononane–N,N',N"–triacetic Acid 1,4,7,10–tetraazacyclododecane–N,N',N",N'"–tetraacetoc Acid", *Inorg. Chem.* (1987) 26:958–960.

Loncin et al., "Coordination of Lanthanides by Two Polyamino Polycarboxylic Macrocycles: Formation of Highly Stable Lanthanide Complexes", *Inorg. Chem.* (1986) 25:2646–2648.

Chang et al., "Dissociation Kinetics of 1,10–Diaza–4,7,13,16–tetraoxacyclooctadecane–N,N'–diacetic Acid Complexes of Lanthanides", *Inorg. Chem.* (1987) 26:1981–1985.

Sessler et al., "A Water–Stable Gadolinium(III) Complex Dervied from A New Pentadentate 'Expanded Porphyrin' Ligand", *Inorg. Chem.* (1989) 28:3390–3393.

Sessler et al., "Expanded Porphyrins", *Top. Cur. Chem.* (1992) 161:177–271.

Dolphin et al., "Porphocyanine: An Expanded Tetrapyrrolic Macrocycle," *J. Am. Chem. Soc.* 115, 9301–9302 (1993); and WO 90/10633 published 20 Sep. 1990.

Marks et al, J. Amer. Chem. Soc., 100:6 pp. 1695–1704, 1978.

LeGoff et al., Tetrahedron Letters; No. 44; pp. 4225–4228., 1978.

excitation wavelength 456 mm
solvent THF
free base porphacyanine excitation wavelength 456mm
Solvent THF + $CH_3COOH$
porphocyanine Cation

METHODS FOR PREPARING PORPHYRIN-LIKE COMPOUNDS

RELATED APPLICATIONS

This application is a continuation-in-part of Ser. No. 07/968,966, filed Oct. 30, 1992, the disclosures of which are incorporated herein by reference.

FIELD OF THE INVENTION

The invention relates to novel expanded wavelength-specific photosensitive porphocyanine and expanded porphyrin-like compounds, novel methods for their preparation and the use of these compounds to mediate the detection or destruction of target cells or tissues by irradiation. Specifically, the invention relates to the preparation of porphocyanine and other porphocyanine-like compounds and derivatives thereof having absorption maxima in the range of 250–850 nanometers and their use to mediate the irradiation of cells or tissues to be detected or destroyed, and to the use of these compounds or conjugates thereof to focus the effects of the irradiation on particular target tissues. In addition, the invention relates to the use of porphocyanine and porphocyanine-like compounds and derivatives thereof in radioimaging and magnetic resonance imaging methods.

BACKGROUND OF THE INVENTION

A considerable effort has been devoted to the synthesis and study of porphyrins and other tetrapyrrolic macrocycles, much less is known about the larger aromatic pyrrole-containing systems, the so-called "expanded porphyrins." Such systems, by virtue of containing a greater number of $\pi$ electrons, additional coordinating heteroatoms and a larger central binding core, may offer advantages over the porphyrins.

The pursuit of these compounds began several decades ago with the first reported synthesis of sapphyrin from tripyrrane dicarboxylic acid and bipyrroledicarboxaldehyde. (Woodward, R. B., Aromaticity Conference, Scheffield, England, 1966; see also, Broadhurst et al., *J. Chem. Soc. Perkins Trans.* (1972) 1:2111 and Bauer et al. (1983) *J. Am. Chem. Soc.* 105:6429). The synthesis of smaragdyrin from bipyrroledicarboxaldehyde and pyrroledipyrromethane dicarboxylic acid was reported in 1970 by M. M. King. (Ph.D. Dissertation, Harvard University, Cambridge, Mass.)

The uranyl complex of superphthalocyanine is another pentapyrrolic macrocyclic compound of historical importance. This compound was prepared by direct template condensation of dicyanobenzene with uranyl dichloride, however, the free base is unstable (Day et al. (1975) *J. Am. Chem. Soc.* 97:4519). Demetalation resulted in contraction of the ring to form phthalocyanine (Marks, T. J. and D. R. Stojakovic (1978) *J. Am. Chem. Soc.* 100:1695).

Gossauer synthesized the first hexaphyrin by condensing a bis-α-tripyrrane with a tripyrrane dialdehyde, followed by oxidation (*Bull. Soc. Chim. Belg.* (1983) 92:793). Of the six methine bridges present in the hexaphyrin, two have E configuration (Id.). Charriere reported that hexaphyrin forms bimetallic complexes with several transition metals (1987, Thesis, University de Fribourg, Suisse). Another hexapyrrolic system, rubyrin, has been recently synthesized and structurally characterized (Sessler et al. (1991a) *Angew. Chem. Int. Ed. Engl.* 30:977).

Vinylogous porphyrins or platyrins are another important class of pyrrole-containing macrocycles first described by R. A. Berger and E. LeGoff (*Tetra. Lett.* (1978) 44:4225; see also, LeGoff, E. and O. G. Weaver (1987) *J. Org. Chem.* 52:711; and Franck et al. (1988) *Proc. SPIE Int. Soc. Opt. Eng.*, Ser. 5, 997:107). These compounds are generally synthesized by reacting a dipyrromethane with a vinylaldehyde-substituted dipyrromethane (Beckman et al. (1990) *Angew. Chem. Int. Ed. Engl.* 29:1395). Bisvinylogous expanded porphyrins were further expanded to tetravinylogous porphyrins in which all four of the normally one atom meso bridges are enlarged. Tetravinylogous porphyrins are made by an acid-catalyzed self-condensation of the N-protected, pyrrole-substituted allyl alcohol. Tetravinylogous porphyrins have a very intense Soret-like band shift of more than 150 nm from that of the normal porphyrins (Gosmann, M. and B. Franck (1986) *Angew. Chem. Int. Ed. Engl.* 25:1100; Knübel, G. and B. Franck (1988) *Angew. Chem. Int. Ed. Engl.* 27:1170). In addition, the synthesis of bisvinylogous porphycene has recently been reported (Jux et al. (1990) *Angew. Chem. Int. Ed. Engl.* 29:1385; Vogel et al. (1990) *Angew. Chem. Int. Ed. Engl.* 29:1387).

Schiff-base compounds represented by texaphyrin are another class of pyrrole containing macrocycles (Sessler et al. (1987) *J. Org. Chem.* 52:4394; Sessler et al. (1988) *J. Am. Chem. Soc.* 110:5586). Texaphyrin is synthesized by acid-catalyzed condensation of tripyrrane dialdehyde with o-phenylenediamine. Several analogs of texaphyrin have been prepared using similar strategies (Sessler et al. (1991b) Abstract of the 201st Natl. Soc. Mtg., Inorganic Division; Sessler et al. (1992) *Inorg. Chem.* 28:529).

The use of porphyrins, combined with irradiation, for the detection and treatment of malignant cells has, by this time, some considerable history. (See, e.g., PORPHYRIN PHOTOSENSITIZATION (Kessel, D. et al., eds. Plenum Press, 1983). Certain porphyrins seem "naturally" capable of localizing malignant cells. When irradiated, porphyrins have two properties which make them useful. First, when irradiated with ultraviolet or visible light, they may fluoresce, and thus be useful in diagnostic methods related to detection of malignancy (see, for example, Kessel et al., supra; Gregory, H. B. Jr. et al., *Ann. Surg.* (1968) 167:827–829).

In addition, when irradiated with ultraviolet (UV), visible, or near-infrared light, certain porphyrins exhibit a cytotoxic effect on the cells in which they are localized (see, for example, Diamond, I. et al., *Lancet* (1972) 2:1175–1177; Dougherty, T. J. et al., *Cancer Research* (1978) 38:2628–2635; Dougherty, T. J. et al., THE SCIENCE OF PHOTO MEDICINE 625–638 (J. D. Regan & J. A. Parrish, eds., 1982); Dougherty, T. J. et al., CANCER: PRINCIPLES AND PRACTICE OF ONCOLOGY 1836–1844 (V. T. DeVita Jr. et al., eds., 1982). Certain of the expanded porphyrins such as sapphyrin, texaphyrin and vinylogous porphyrins possess unique long-wavelength and singlet oxygen producing properties which make them attractive as potential photosensitizers for use in tumor phototherapy (Maiya et al. (1990) *J. Phys. Chem.* 94:3597; Sessler et al. (1991c) *SPIE Soc.* 1426:318; Franck et al., supra).

While the conjugation of certain porphyrins, such as hematoporphyrin, to immunoglobulins specific for targeted cells may refine the ability of certain porphyrins to home to the desired cells or tissue, this still does not solve another problem ancillary to this general therapeutic approach, namely that the wavelength for irradiation required to activate certain porphyrins, which is in the range of 630 nanometers, is also an energy which is readily absorbed by other porphyrins and natural chromophores normally present in the blood and other tissues. Therefore, the depth of the effective treatment has been limited to a few millimeters because of blocking effects of light-absorbing natural chromophores such as hemoglobin. Accordingly, it would be desirable to administer compounds to mediate the effects of irradiation which can be excited at longer wavelengths thus avoiding the blocking effects of natural chromophores present throughout the subject organism.

In addition to phototherapy, expanded porphyrins are useful in magnetic resonance imaging (MRI). MRI is a noninvasive, non-ionizing method that allows normal and abnormal tissue to be observed and recognized at the early stages of development. At this time MRI has a significant drawback, however, in that the degree of signal enhancement for diseased versus normal tissues is often insufficient to allow this method to be used in many clinical situations. To overcome this problem, considerable effort is underway to develop contrast reagents for MRI. Paramagnetic metal complexes, such as those derived from gadolinium(III) (Gd) have recently proven particularly efficient in clinical trials.

To date, the coordination of gadolinium in MRI contrast agents has been achieved using carboxylate-type ligands. (See, for example, Lauffer, R. B. (1987) *Chem. Rev.* 87:901; Kornguth et al. (1987) *J. Neursurg.* 66:898; Koenig et al. (1986) *Invest. Radiol.* 21:697; Chacheris et al. (1987) *Inorg. Chem.* 26:958; Loncin et al. (1986) *Inorg. Chem.* 25:2646; Chang, C. A. and V. C. Sekhar (1987) *Inorg. Chem.* 26:1981). The known systems are all of high thermodynamic stability but high intrinsic lability. Certain expanded porphyrins, on the other hand, can form stable complexes with Gd(III) which does not form stable complexes with normal porphyrins. As a result, they provide an improved approach as MRI contrast agents. Sessler et al. reported that texaphyrin forms an extremely stable Gd(III) complex in vitro (Sessler et al. (1989) *Inorg. Chem.* 28:3390). In addition to Gd(III), texaphyrin has been reported to form complexes with a variety of transition metals such as Cd and Eu (Sessler, J. L. and A. K. Burrell (1992) *Top. Cur. Chem.* 161:177).

DISCLOSURE OF THE INVENTION

The invention provides novel light-absorbing compounds suitable for use in detecting and/or treating target tissues, cells and pathogens. The invention also provides for novel methods for preparing the novel expanded porphyrins (porphocyanines), which either increase the yield of the porphocyanine or greatly simplify the synthetic process. These compounds may be administered in relatively low dosage due to their capability to absorb radiation in an energy range outside of that normally absorbed by the components present in high concentration in blood or other tissues, in particular the porphyrin residues normally associated with hemoglobin and myoglobin. Therefore, by providing these novel expanded porphyrin-like compounds with higher wavelengths of activation, the irradiation treatment can be conducted at a wavelength at which the native chromophores do not compete for photons with the active compounds. This results in greater depth of penetration of the light. These compounds are preferentially retained in target tissues and cells as compared to non-target tissues and cells. Accordingly, when labeled with or conjugated to a radioisotope or paramagnetic ion porphocyanine and porphocyanine-like compounds are particularly useful as radioimaging and magnetic resonance image contrast agents, respectively. In addition, the increased stability of the available metal-binding core and the greater number of atoms available to bind the metals render porphocyanine and porphocyanine-like compounds particularly useful as magnetic resonance contrast agents. Another advantage of porphocyanine and the other novel porphocyanine-like compounds of the present invention and conjugates thereof comprising a metallic element is their ability to luminesce when exposed to UV, visible or near infrared radiation. Thus, these compounds are particularly useful for detecting lesions and tumors. This collection of fluorescent derivatives is referred to herein as "porphocyanine" and "porphocyanine-like compounds."

Porphocyanine is exemplified by the compound of Formula I, wherein R is a non-interfering substituent including, but not limited to, the group consisting of substituted and unsubstituted alkyl, alkenyl, alkynl; substituted and unsubstituted aryl; alkyl or aryl sulfonyl; alkyl or aryl cyano; halogen; cyano; nitro; amino; carboxy; carbalkoxy or the ester, amide or salt thereof and the like.

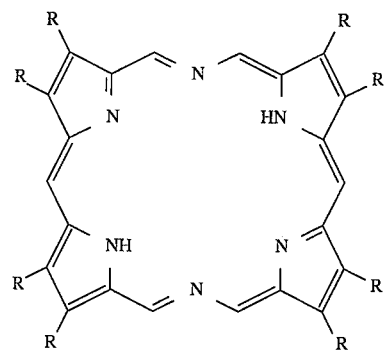

As used herein, carboxy is, as conventionally defined, —COOH, and carbalkoxy is —COOR, wherein R is alkyl (1–6C). As used herein, alkyl is a saturated straight or branched chain hydrocarbon of 1–6 carbon atoms such as methyl, ethyl, 2-methylpentyl, t-butyl, n-propyl, and so forth.

Aryl (6–10C) is phenyl optionally substituted with 1–3 substituents independently selected from halo (fluoro, chloro, bromo or iodo), lower alkyl (1–4C) or lower alkoxy (1–4C). Alkoxy is —OR wherein R is alkyl as herein defined.

The aryl (6–10C) or alkyl (1–6C) sulfonyl moieties have the formula $SO_2R$ wherein R is alkyl or is aryl as above-defined.

The invention compounds also include the salts, esters and amides of —COOH. For use in vivo these salts, esters and amides must be pharmaceutically acceptable and nontoxic; this requirement in not germane to in vitro use. "Salts, esters, and amides" refers to salts derived from inorganic or organic bases, including pharmaceutically acceptable nontoxic inorganic and organic bases, and alkyl esters or amides derived from alcohols or primary or secondary amines of the formula ROH or $RNH_2$ or $R_2NH$ wherein R is alkyl as herein defined. suitable inorganic bases include sodium, potassium, lithium, ammonium, calcium, and magnesium, hydroxides, and the like. Particularly preferred are the potassium and sodium salts. Pharmaceutically acceptable organic nontoxic bases include primary, secondary, tertiary and quaternary amines including cyclic amines, and basic ion-exchange resins. Examples include isopropylamine, trimethylamine, ethanolamine, dicyclohexylamine, lysine, arginine, histidine, caffeine, procaine, choline, betaine, glucosamine, theobromine, purines, piperazine, polyamine resins, and the like.

The salt derivatives are prepared by treating the free acids with an appropriate amount of pharmaceutically acceptable base. The reaction can be conducted under anhydrous conditions or in water, alone or in combination with an inert, water-miscible organic solvent, at a temperature of from about 0° C. to about 100° C., preferably at room temperature at a suitable molar ration of invention compound to base. Typical inert, water-miscible organic solvents include methanol, ethanol, isopropanol, butanol, acetone, dioxane or tetrahydrofuran.

The salt derivatives can be reconverted to their respective free acids by acidifying with an acid, preferably an inorganic acid, e.g., hydrochloric acid, sulfuric acid and the like, at a temperature of from about 0° C. to about 50° C., preferably at room temperature.

The esters are prepared by esterifying the corresponding free acids with an alcohol reagent corresponding to the desired ester. This reaction is conducted in the presence of a strong acid, such as boron trifluoride, hydrogen chloride, sulfuric acid, p-toluenesulfonic acid, and the like. Since the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichloroethane; or an ether solvent, e.g., diethyl ether, dibutyl ether, dioxane, tetrahydrofuran, and the like. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent such as diethyl ether, benzene, methylene chloride, and the like, combining the extracts, washing the extracts with water to neutrality, and then evaporating under reduced pressure.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by transesterification to the ethyl ester.

In still another alternative, the ester can be prepared by reacting the free acid form with the appropriate diazo alkane, such as diazomethane, diazo-n-hexane, or diazo-i-propane in an aprotic organic solvent at low temperature.

The amides are obtained by activation of the carboxylic acid residue, for example by thioxylchloride, and treating with the appropriate amine.

Examples of target cells and tissues within the present invention include, but are not limited to, tumors, including blood tumors, malignant bone marrow, virally-infected blood cells or bone marrow, dysplastic cells or tissues, sites of inflammation or infection, hyperproliferative tissue such as psoriatic plaque or papillomavirus lesions (warts) or neointimal hyperplasia lesions, hypervascularization such as portwine stains and hemangiomas, atherosclerotic plaque, hair follicles, free viruses, bacteria, protozoa or other pathogenic parasites.

In still another aspect, the invention relates to a method for inactivating certain viruses, bacteria, protozoa and other pathogenic parasites using porphacyanine and/or the porphacyanine-like compounds. Targeted pathogens contemplated by the present invention include enveloped viruses such as human cytomegaloviruses, Epstein-Barr virus, Marek's disease herpes virus, human herpes simplex viruses, varicella-zoster virus, members of the family Poxviridae, members of the family Hepadnaviridae such as human hepatitis A virus (HAV), human hepatitis B virus (HBV) and non-A, non-B hepatitis viruses, including human hepatitis C virus, members of the family Orthomyxoviridae such as influenza virus types A, B and C, members of the family Retroviridae such as human T cell leukemia viruses, human immunodeficiency viruses, and members of the family Flaviviridae such as tick-borne encephalitis virus or yellow fever virus.

Another class of pathogen contemplated by the present invention includes parasites such as *Plasmodium malariae, P. falciparum, P. ovale, P. vivax* and *Trypanosoma cruzi*.

The eradication of bacteria is also contemplated by the present invention including *Bacillus subtills, Streptococcus faecalis, Pseudomonas spp., Mycobacterium spp.* and other opportunistic organisms treatable by photodynamic activation.

In addition, porphocyanine and porphocyanine-like compounds within the present invention can be conjugated to target-specific moieties (Tsm) such as immunoglobulins including polyclonal and monoclonal antibodies and fragments thereof, H2-agonists, steroids including estrogen and testosterone, sugars such as mannose and peptides such as T-cell receptors and alpha-beta heterodimers. Conjugation of porphocyanine and porphocyanine-like compounds to Tsms may facilitate their concentration in a desired target tissue.

Thus, in one aspect, the invention relates to a conjugate of the formula Tsm-L-Pc where Tsm represents a target-specific moiety such as an immunoglobulin or a hormone, Pc represents a porphocyanine derivative having an absorption maximum in the range of 400–850 nanometers, and L represents either a covalent bond linking these components or a linking moiety covalently linked to each of the Tsm and Pc.

Preferably, the Pc is selected from a group consisting of porphocyanine and porphocyanine-like derivatives obtained using methods to cyclize mono-, di and oligo-pyrrolic precursors to give macrocycles containing

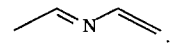

In other aspects, the invention relates to methods for effecting cytotoxicity against target cells using porphocyanine and porphocyanine-like compounds in the presence of UV, visible or near infrared light either alone or as the conjugates described above.

In yet additional aspects, the invention relates to methods for detecting diseased tissues using porphocyanine and porphocyanine-like compounds or conjugates thereof. Porphocyanine and the porphacyanine-like compounds of the present invention can be labeled with or conjugated to a radioisotope for radioimaging (scintigraphic imaging) or a magnetic resonance image enhancing agent, for use as a diagnostic imaging agent. Examples of radioisotopes which would be useful labels for porphocyanine and porphocyanine-like compounds include Iodine-123, Iodine-131, Technetium-99m, Indium-111 and gallium-67. Examples of compounds which would be useful for MRI imaging enhancement when conjugated to porphocyanine and porphocyanine-like compounds include paramagnetic ions of elements such as Gd, Mn, Eu, Dy, Pr, Pa, Cr, Co, Fe, Cu, Ni, Ti, and V.

In further aspects, the invention relates to pharmaceutical compositions containing these active ingredients.

MODES OF CARRYING OUT THE INVENTION

Porphacyanine and the Porphacyanine-like Compounds

Figure 1:
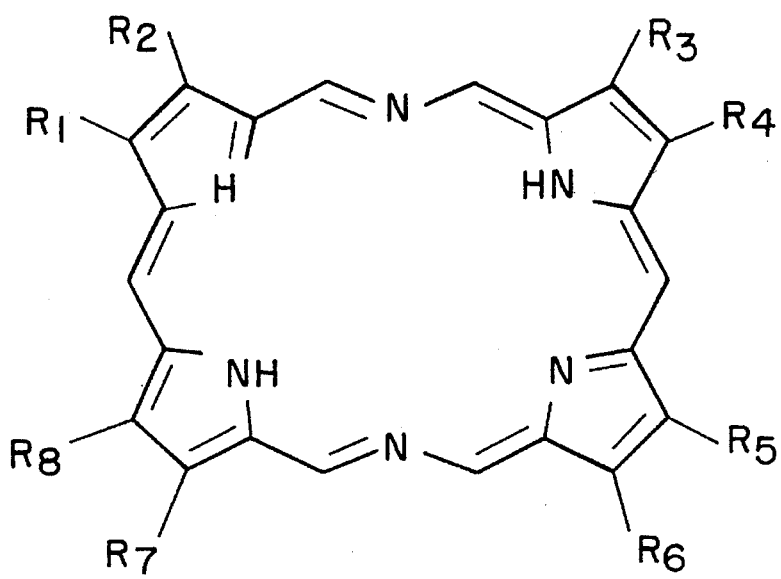
FIG. 1 shows the structure of a porphocyanine of Formula I.

All of the compositions of the invention employ as the light-absorbing compounds novel expanded porphyrin-like macrocycle derivatives, namely porphocyanine and porphocyanine-like compounds, which have a light absorption maximum in the range of 400–850 nanometers. Porphocyanine and porphocyanine-like compounds are macrocycles wherein at least one of the of known polypyrrolic macrocycles is replaced by an

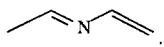

Specific preparation of a porphocyanine useful in the invention is achieved by adding lead tetraacetate to 2-benzyloxycarbonyl-3,4-diethyl-5-methyl pyrrole in glacial acetic acid. Ethylene glycol is added to reduce any remaining Pb(IV). Water is added and the 5-acetoxymethyl-2-benzyloxycarbonyl-3,4-diethylpyrrole (Compound A in FIG. 2) is collected by filtration and washed with additional water. The 5-acetoxymethyl-2-benzyloxycarbonyl-3,4-diethylpyrrole is added to acetic acid in water and heated. The solid product, is precipitated as large chunks when the foregoing solution cools to room temperature. Water is added and the product is collected by filtration and then washed with additional water. The filtrate is extracted with $CH_2Cl_2$ and then evaporated to produce a solid product. The solid products are combined, and then recrystallized from a solution of $CH_2Cl_2$ and hexanes.

5,5'-bis(benzyloxycarbonyl)-3,3'-4,4'-tetraethyl-2,2'-dipyrromethane (Compound B of FIG. 2) in tetrahydrofuran (THF) is stirred under hydrogen in the presence of Pd/C and triethylamine. After the catalyst is filtered through celite, the filtrate is evaporated to dryness resulting in dicarboxylic acid. The dicarboxylic acid is dissolved in N,N-dimethylformamide and heated to boiling under argon. The solution is chilled and an excess of chilled benzoyl chloride is added to the bis-α-free dipyrromethane (Compound B). The reaction mixture is stirred and the solid product collected by filtration. The solid product is added to water and basified using $NaHCO_3$ and heated to 60° C. The pale yellow product crystallizes from the solution and is filtered and washed with water.

3,3',4,4'-tetraethyl-5,5'-diformyl-2,2'-dipyrromethane (Compound C of FIG. 2) in ethanol is bubbled with argon and then hydroxylamine hydrogen chloride and sodium acetate are added. This mixture is heated under argon and then the solvent is removed and the product dried overnight in vacuo. The bis-oxime is dissolved in acetic anhydride and saturate with argon. The crude bisnitrile product (Compound D of FIG. 2) is obtained as a black solid after removal of acetic anhydride and dried under vacuum. The product is purified by silica gel column with 0.5% methanol in $CH_2Cl_2$, followed by an alumina column with 10–20% EtOAc. Evaporation of the solvent yields 3,3'-4,4'-tetraethyl-5,5'-cyanodipyrromethane as pale pink crystals.

In one embodiment (FIG. 2), the 3,3'-4,4'-tetraethyl-5,5'-cyanodipyrromethane is then dissolved in THF and added to a THF suspension of $LiAlH_4$. The resulting mixture is stirred and water is added. A solid product forms which is filtered off. The bis-amine product is obtained after evaporation of the solvent by drying under vacuum. The bis-amine is dissolved in anhydrous methanol and bis-aldehyde is added. The solution is bubbled and brought to reflux with nitrogen. Lead thiocyanate ($Pb(SCN)_2$) is added and the solution is refluxed. Oxygen gas is bubbled through the solution at room temperature. After evaporation of the solvent, the crude porphacyanine product is dried under vacuum. The product is purified by $Al_2O_3$ column with ethyl acetate in $CH_2Cl_2$. The green eluent is collected and concentrated. Crystals of the porphocyanine macrocycle are obtained after evaporation of the solvent.

In an alternative embodiment (FIG. 3), the 3,3'-4,4'-tetraethyl-5,5'-cyanodipyrromethane in anhydrous THF is added to a THF suspension of $LiAlH_4$ under nitrogen at 0° C. The mixture is stirred and water is added to quench the reaction and the precipitate is filtered off. The golden colored solution is transferred to a two-neck flask containing equimolar portions of $Pb(SCN)_2$ and anhydrous sodium sulphate. Anhydrous methanol is added and the mixture is brought to reflux. The color gradually changes from purple to dark green. The reaction is stopped and air is bubbled slowly through the solution. The crude product was dissolved in methylene chloride and the solid was filtered off.

The volume of the green solution is reduced to approximately 5 ml and then charged on an alumina column and eluted with ethylacetate in $CH_2Cl_2$. The bright green eluent containing the porphacyanine is collected and evaporated to dryness.

In yet another alternative (FIG. 4), the unique linking group

Figure 4:
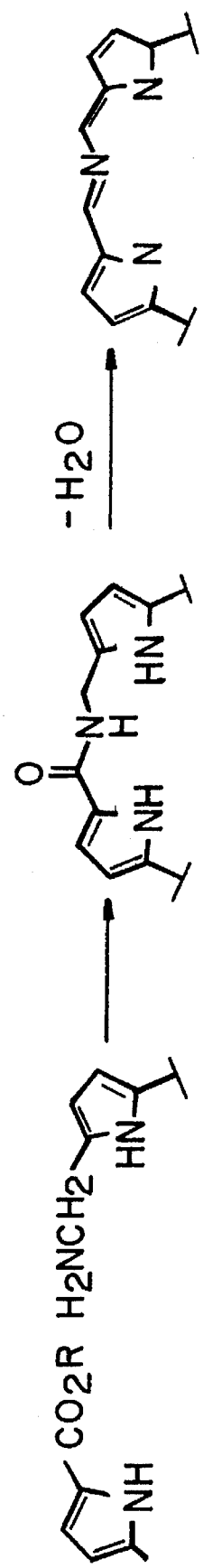
FIG. 4 illustrates yet another method for synthesizing a porphocyanine of Formula I.
Figure 5:
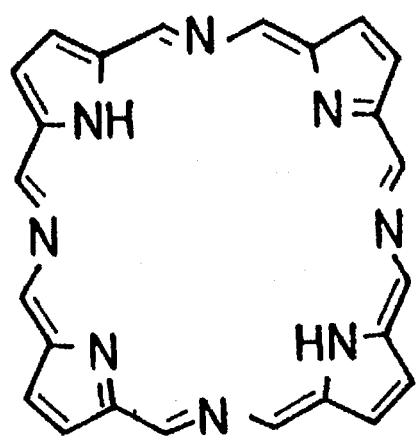
FIG. 5 shows the structure of a porphocyanine-like compound within the present invention.
Figure 6:
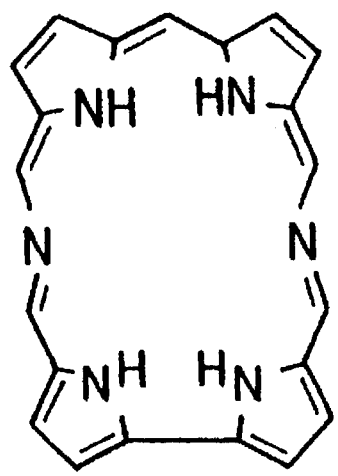
FIG. 6 shows the structure of another porphacyanine-like compound within the present invention.
Figure 7:
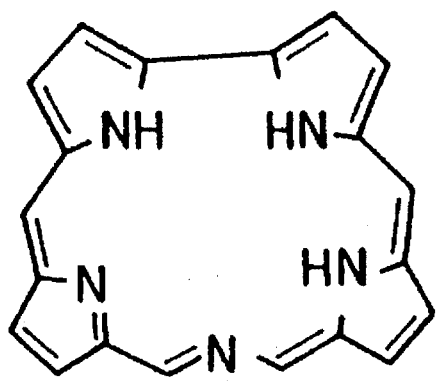
FIG. 7 shows the structure of yet another porphacyanine-like compound within the present invention.
Figure 8:
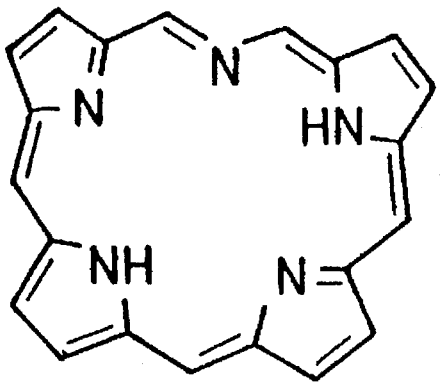
FIG. 8 shows the structure of still another porphacyanine-like compound within the present invention.
Figure 9:
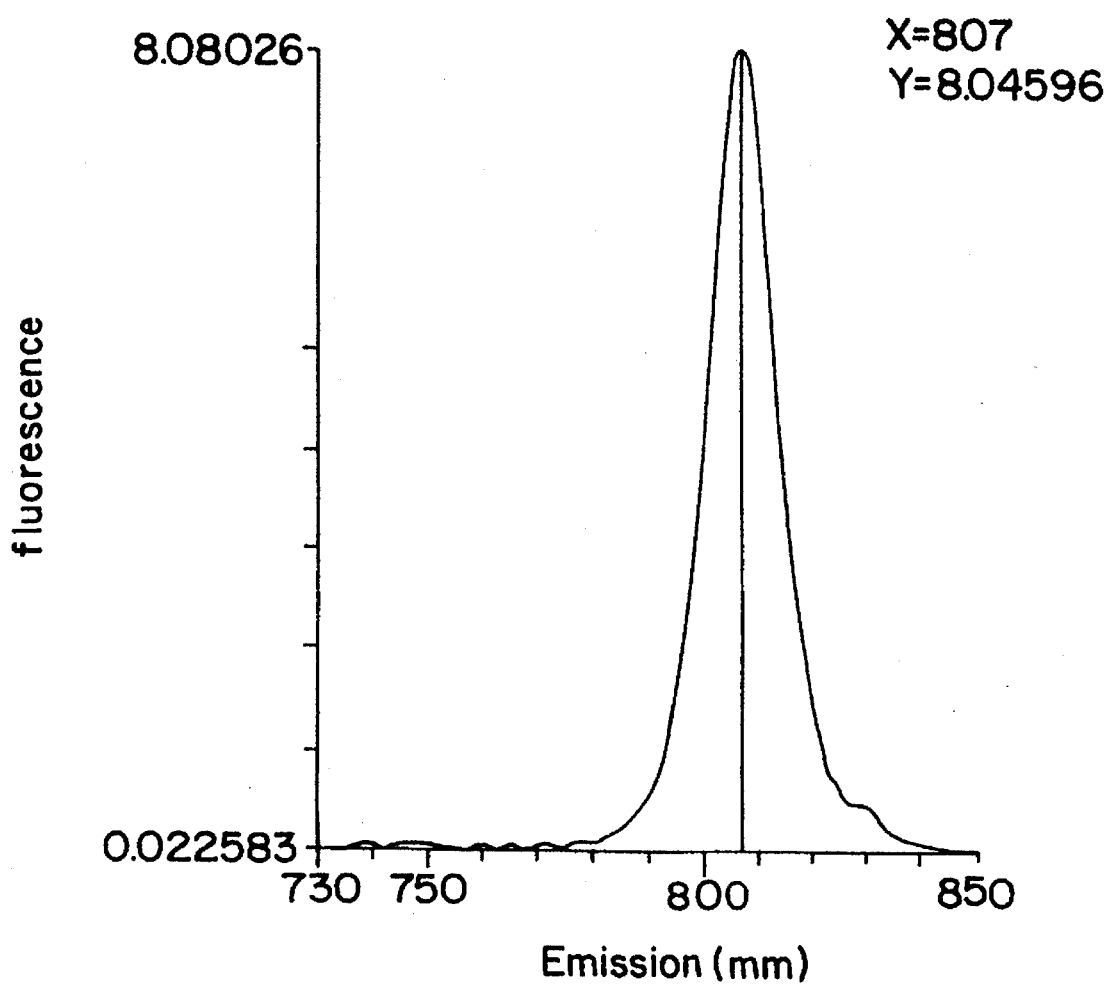
FIG. 9 illustrates the emission wavelength of the free base of a porphocyanine of Formula I when excited at 456 nm.
Figure 10:
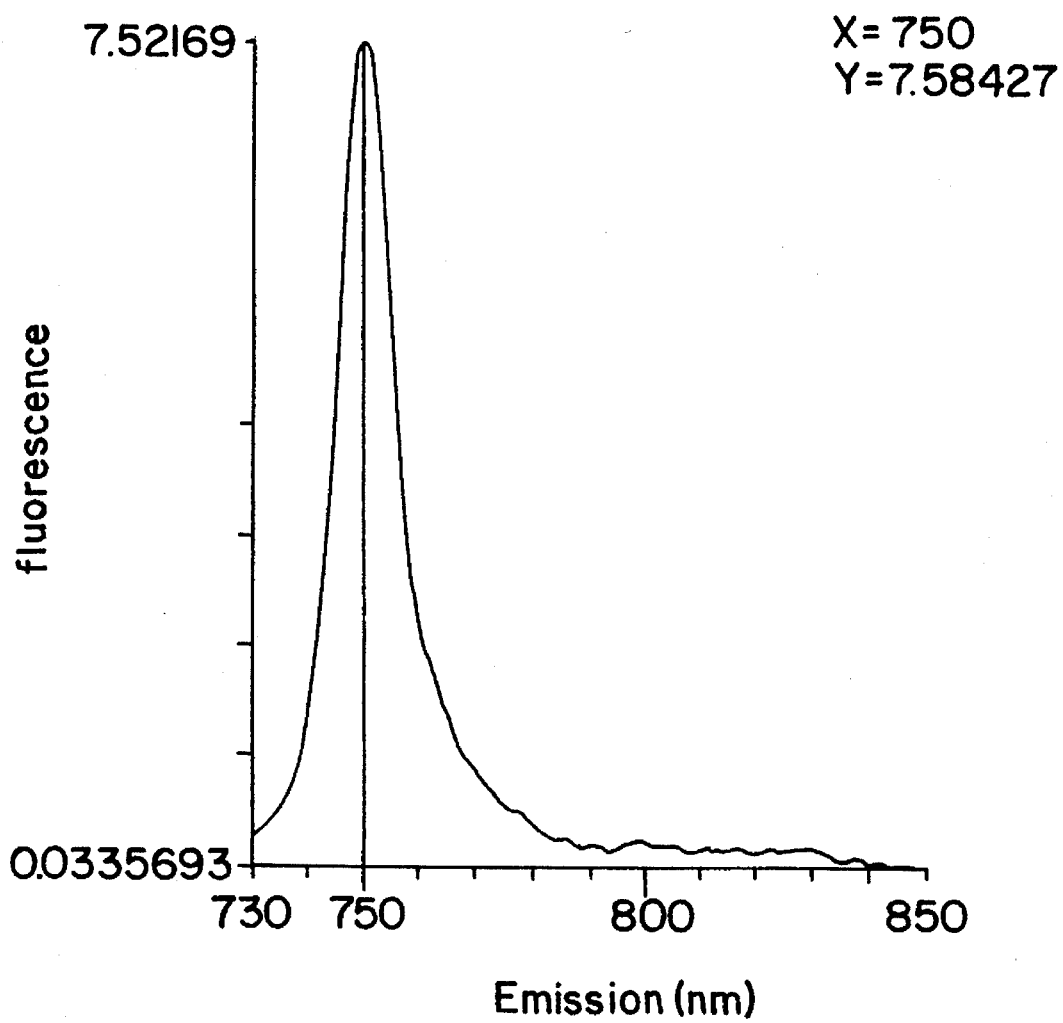
FIG. 10 illustrates the emission wavelength of a protonated porphocyanine of Formula I when excited at 456 nm.

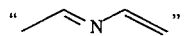

is formed by preforming and dehydrating an amide linkage as shown in FIG. 4.

Thus, there are obtained compounds shown as Formula I of FIG. 1 wherein each R can independently be substituted or unsubstituted alkyl, alkenyl, alkynl; substituted or unsubstituted aryl; alkyl or aryl sulfonyl; alkyl or aryl cyano; halogen; cyano; nitro; amino; carboxy; carbalkoxy or the ester, amide or salt thereof and the like.

In a novel method for preparing a porphocyanine of Formula I (FIG. 11), the 3,3'-4,4'-tetraethyl-5,5'-cyanodipyrromethane in anhydrous THF is added to a THF suspension of $LiAlH_4$ under nitrogen at 0° C. The mixture is stirred and water is added to quench the reaction and the precipitate is filtered off. A ten-fold excess of 2,3-dichloro-5,6-dicyano-1,4-benzoquinone (DDQ) in a $THF/CH_2Cl_2$ suspension under nitrogen at 0° C. is added to the 3,3'-4,4'-tetraethyl-5,5'-bisaminomethyl-2,2'-dipyrromethane in anhydrous $THF/CH_2Cl_2$. The solution turns dark green immediately. The crude product is dissolved in methylene chloride and the solid filtered off. The volume of the green solution is reduced to approximately 5 ml and then charged on an alumina column and eluted with ethylacetate in $CH_2Cl_2$. The bright green eluent containing the porphocyanine is collected and evaporated to dryness. A significant increase in yield (48%) is obtained from this synthetic process as compared to the yield obtained via air oxidation.

Figure 12:
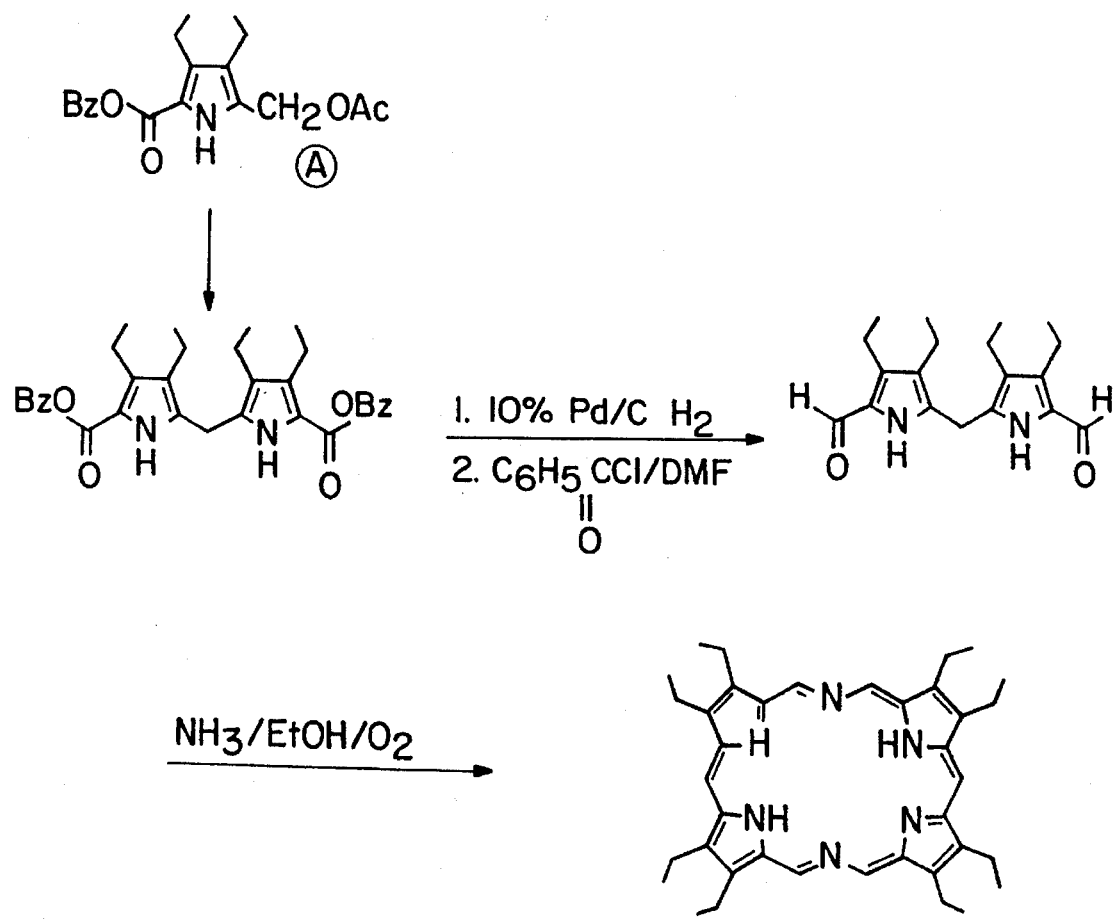
FIG. 12 illustrates a novel, simplified method for synthesizing a porphocyanine of Formula I.

In another novel method for preparing a porphocyanine of Formula I (FIG. 12,) 3,3'-4,4'-tetraethyl-5,5'-diformyl-2,2'-dipyrromethane is suspended in dry EtOH. The resulting ethanol solution is chilled at 0° C. and ammonia gas is bubbled through it. The flask is then placed in an oil bath at 60° C. for 72 hours. The reaction is stopped and cooled at 0° C. Ethanol is removed on the roto-vap, the residue is chromatographed on neutral Alumina with dichloromethane. This greatly simplified synthetic process yields 20% or 4.6 mg of octaethylporphocyanine. Another 1.5 mg of product is obtained from the oxidation of the more polar component by DDQ.

Figure 13:
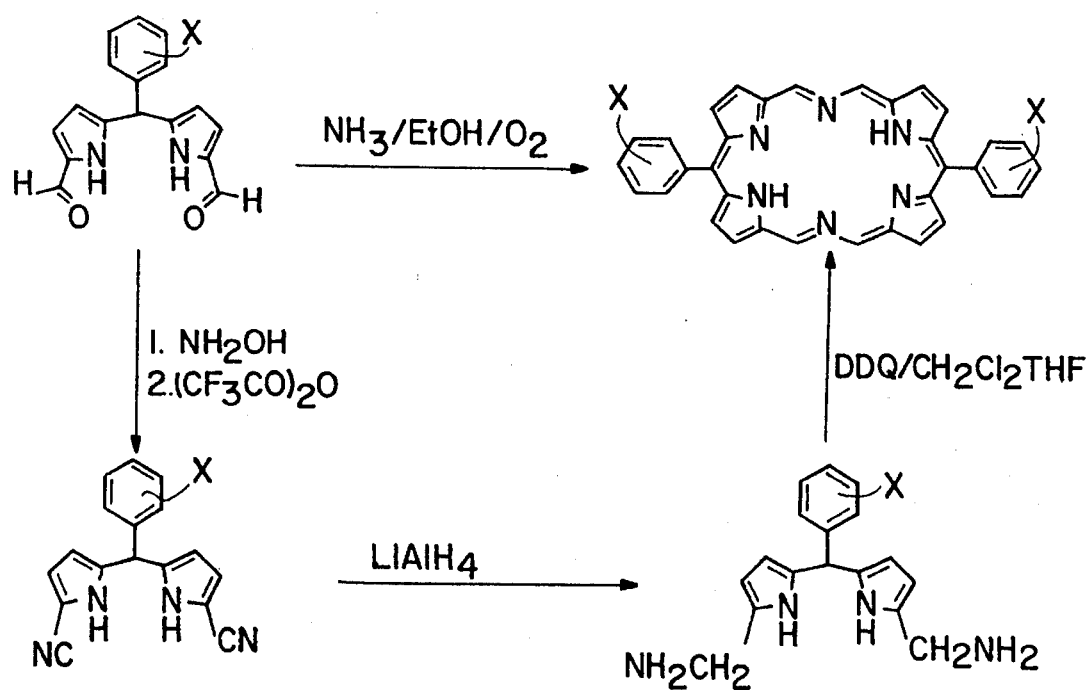
FIG. 13 illustrates a novel method for synthesizing porphocyanines within the present invention containing substituted or unsubstituted phenyl groups on the two bridge carbon atoms.

In yet another embodiment, porphocyanines containing a phenyl group on each of the two bridge carbon atoms are prepared by the reaction scheme shown in FIG. 13. Thus, there are obtained compounds shown in FIG. 13 wherein each X can independently be substituted or unsubstituted alkyl, alkenyl, alkynl; substituted or unsubstituted aryl; alkyl or aryl sulfonyl; alkyl or aryl cyano; halogen; cyano; nitro; amino; carboxy; carbalkoxy or the ester, amide or salt thereof and the like.

Figure 14:
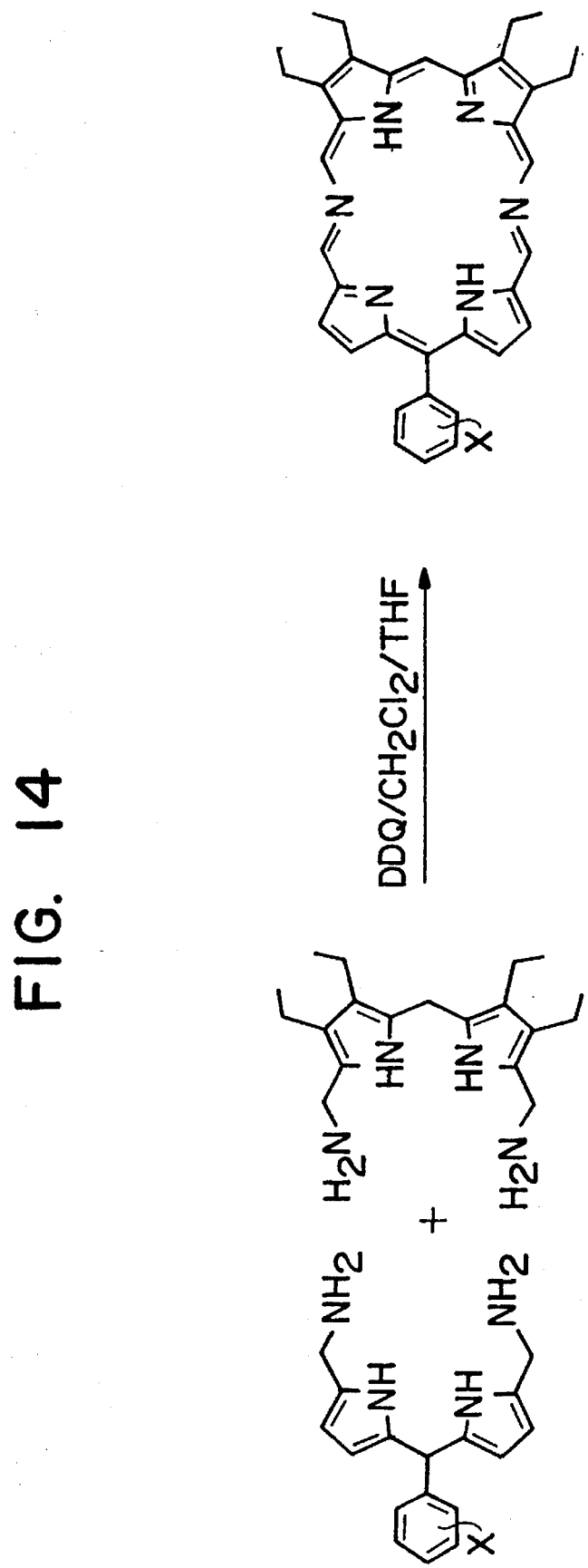
FIG. 14 illustrates a novel method for synthesizing asymetrical porphocyanines within the present invention containing a substituted or unsubstituted phenyl groups on one of the two bridge carbon atoms.

In still another embodiment, porphocyanines containing a phenyl group on one of the two bridge carbon atoms are prepared by the reaction scheme shown in FIG. 14.

Target-Specific Moieties

Porphocyanine and the porphocyanine-like compounds alone are particularly useful as targeting agents in that they specifically localize to certain diseased tissues and cells such as tumors. This targeting ability may be enhanced by coupling a porphocyanine to certain moieties that specifically bind to epitopes or receptors located on the surface of such tissues or cells. Thus, target-specific moieties within the present invention include steroids such as estrogen and testosterone and derivatives thereof, peptides comprising T-cell receptors or alpha-beta heterodimers, saccharides such as mannose for which monocytes and macrophages have receptors and H2 agonists.

Target-specific moieties which comprise a component of conjugates within the present invention may also consist of immunospecific components. The Tsm may be derived from polyclonal or monoclonal antibody preparations and may contain whole antibodies or immunologically reactive fragments of these antibodies such as $(F(ab^1)_2$, Fab, or Fab' fragments. Use of such immunologically reactive fragments as substitutes for whole antibodies is well known in the art. See, for example, Spiegelberg, H. L., *Immunoassays in the Clinical Laboratory* (1978) 3:1–23.

Polyclonal antisera are prepared in conventional ways by injecting a suitable mammal with antigen to which antibody is desired, assaying the antibody level in serum against the antigen, and preparing antisera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies exemplified herein include the monoclonal antibody preparation CAMAL-1 which can be prepared as described by Malcolm et al. (*Ex. Hematol.* (1984) 12:539–547); polyclonal or monoclonal preparations of anti-M1 antibody as described by Mew et al., (*J. Immunol.* (1983) 130:1473–1477) and B16G antibody which is prepared as described by Maier et al. (*J. Immunol.* (1983) 131:1843) and Steele et al. (*Cell Immunol.* (1984) 90:303).

The foregoing list is exemplary and certainly not limiting; once the target tissue is known, antibody specific for this tissue may be prepared by conventional means. Therefore, the invention is applicable to effecting toxicity against any desired target.

Linkage

Conjugation of the target-specific moiety to a porphacyanine within the present invention can be effected by any convenient means and requires that at least one of $R_1-R_8$ contain a carboxylic group. A direct covalent bond between these moieties may be effected, for example, using a dehydrating agent such as a carbodiimide, in which case L represents a covalent bond. A particularly preferred method of covalently binding a porphacyanine to the target-specific moiety is treatment with 1-ethyl-3-(3-dimethylaminopropyl) carbodiimide (EDCI) in the presence of a reaction medium consisting essentially of dimethylsulfoxide (DMSO). A preparation using this preferred procedure is illustrated in Example 5 below.

Of course, other dehydrating agents such as dicyclohexylcarbodiimide or diethylcarbodiimide could also be used as well as conventional aqueous and partially aqueous media.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

Administration and Use

The porphocyanine or conjugates thereof are formulated into pharmaceutical compositions for administration to the subject using techniques known in the art generally. A summary of such pharmaceutical compositions may be found, for example, in REMINGTON'S PHARMACEUTICAL SCIENCES (Mack Publishing Co., Easton, Pa., latest edition).

Porphocyanine, porphocyanine-like compounds and conjugates thereof within the present invention would normally be administered systemically, in particular by injection. Injection may be intravenous, subcutaneous, intramuscular, or even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in REMINGTON'S PHARMACEUTICAL SCIENCES (supra).

If the treatment is to be localized, such as for the treatment of superficial tumors or skin disorders, porphocyanine, porphocyanine-like compounds or the active conjugates thereof may be topically administered using standard topical compositions involving lotions, suspensions, pastes, or creams.

The quantity of conjugate or porphocyanine derivative to be administered depends on the choice of active ingredient, the condition to be treated, the mode of administration, the individual subject, and the judgment of the practitioner. Depending on the specificity of the preparation, smaller or larger doses may be needed. Dosages in the range of about 0.05–10 mg/kg are suggested for systemic administration. Dosages in the range of about 0.01–20% concentration of active ingredient, preferably 1–5%, are suggested for topical administration. A total daily dosage in the range of about 10–300 mg are suggested for oral administration. The foregoing ranges are merely suggestive, as the number of variables in regard to an individual treatment regime is large and considerable excursions from these recommended values are expected.

The radioimaging (scintigraphic imaging) method of the present invention is practiced by injecting an individual parenterally with an effective amount of the porphocyanine radioimaging agent. By parenterally is meant, e.g., intravenously, intraarterially, intrathecally, interstitially or intracavitarily. It is contemplated that an individual will receive a dosage of from about 1 mCi to 50 mCi of the radioimaging agent, the amount being a function of the particular radioisotope and mode of administration. For intravenous injection, the amount are normally: about 10–40 mCi, preferably about 20 mCi of Tc-99m; about 2–5 mCi, preferably about 4 mCi of In-111 or Ga-67.

The radioimaging agent is conveniently provided as an injectable preparation, preferably a sterile injectable preparation for human use, for targeting the agent to diseased tissue or cells, preferably comprising: a sterile injectable solution containing an effective amount of the radiolabeled agent in a pharmaceutically acceptable sterile injection vehicle, preferably phosphate buffered saline (PBS) at physiological pH and concentration. Other pharmaceutically acceptable vehicles may be utilized as required for the site of parenteral administration.

A representative preparation to be parenterally administered in accordance with this invention will normally contain about 0.1 to 20 mg, preferably about 2 mg, of radiolabeled agent in a sterile solution.

Once enough isotope has been deposited at the target site, scanning is effected with either a conventional planar and/or SPECT gamma camera, or by use of a hand held gamma probe used externally or internally to localize the inflammation or the lesion. The scintigram is normally taken by a gamma imaging camera having one or more windows for detection of energies in the 50–500 KeV range.

Magnetic resonance imaging (MRI) is effected in an analogous method to radioimaging except that the imaging agents will contain MRI enhancing species rather than radioisotopes. It will be appreciated that the magnetic resonance phenomenon operates on a different principle from radioimaging. Normally the signal generated is correlated with the relaxation times of the magnetic moments of protons in the nuclei of the hydrogen atoms of water molecules in the region to be imaged. The magnetic resonance image enhancing agent acts by increasing the rate of relaxation, thereby increasing the contrast between water molecules in the region where the imaging agent accretes and water molecules elsewhere in the body. However, the effect of the agent is to increase both $T_1$ and $T_2$, the former resulting in greater contrast, while the latter results in lesser contrast. Accordingly, the phenomenon is concentration dependent, and there is normally an optimum concentration of a paramagnetic species for maximum efficiency. The optimum concentration will vary with the particular agent used, the locus of imaging, the mode of imaging, i.e., spin-echo, saturation-recovery, inversion-recovery and for various other strongly $T_1$ dependent or $T_2$ dependent imaging techniques, and the composition of the medium in which the agent is dissolved or suspended. These factors, and their relative importance are known in the art. See, e.g., Pykett, *Scientific American* (1982) 246:78, and Runge et al., *Am. J. Radiol.* (1987) 141:1209.

The MRI method of the invention is practiced by injecting an individual parenterally with an effective amount of an MRI contrast agent comprising porphacyanine or a porphacyanine-like compound within the present invention coupled to a metallic element such as gadolinium. It is contemplated that an individual will receive a dosage of contrast agent sufficient to enhance the MRI signal at the targeted site by at least about 20%, preferably 50–500%, the amount being a function of the particular paramagnetic species and the mode of administration.

Again, a contrast agent within the present invention is conveniently provided as an injectable preparation for use, preferably a sterile injectable preparation for human use, for targeting an MRI agent to diseased tissues or cells, preferably comprising: a sterile injectable solution containing an effective amount of the contrast agent in a pharmaceutically acceptable sterile injection vehicle, preferably phosphate buffered saline. Other conventional pharmaceutically acceptable vehicles for parenteral administration may be utilized as required for the site of parenteral administration.

A representative preparation to be parenterally administered in accordance with this invention will normally contain about 0.1 to 20 mg, preferably about 2 mg of contrast agent, in a sterile solution.

EXAMPLES

The following examples are intended to illustrate the invention but not to limit it scope.

EXAMPLE 1

Figure 2:
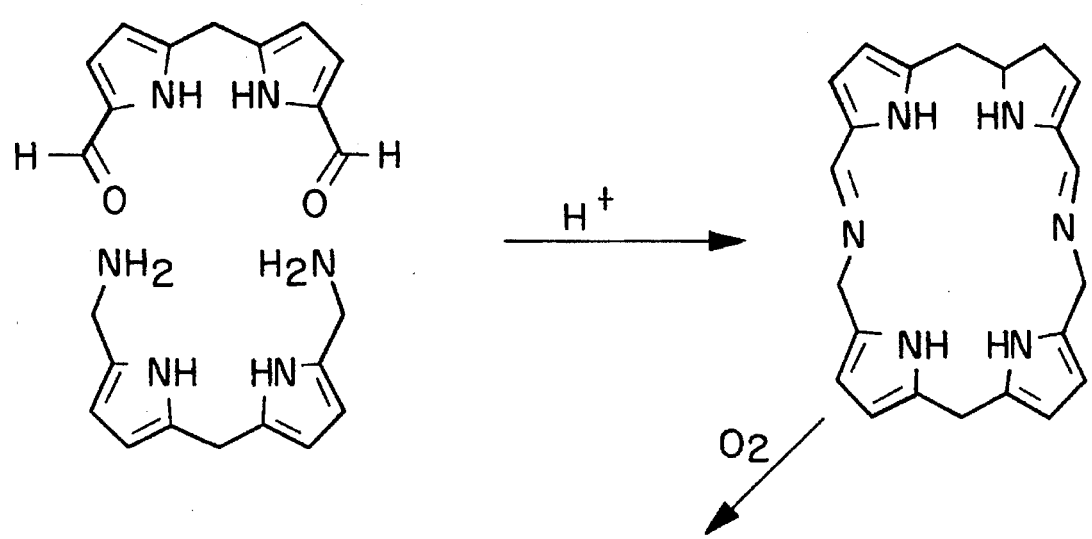
FIG. 2 illustrates one method for synthesizing a porphocyanine of Formula I.

Synthesis of Porphocyanine, FIG. 2

Lead tetraacetate (18.2 g, 0.041 mole) was added to a stirred solution of 2-benzyloxycarbonyl-3,4-diethyl-5-methyl pyrrole (10.1 g, 0.037 mole) in 60 ml glacial acetic acid. The mixture was warmed briefly to 60° C. Ten milliliters of ethylene glycol was added to reduce any remaining Pb(IV). Twenty milliliters of water was added and the 5-acetoxymethyl-2-benzyloxycarbonyl-3,4-diethylpyrrole (Compound A in FIG. 2) was collected by filtration and washed with additional water. The 5-acetoxymethyl-2-benzyloxycarbonyl-3,4-diethylpyrrole was added to 80% acetic acid in 100 ml water and heated at 100° C. for one hour. The solid product precipitated as large chunks when the foregoing solution cooled to room temperature. One hundred milliliters of water was added and the product was collected by filtration and then washed with additional water. The filtrate was extracted with $CH_2Cl_2$ and then evaporated to produce a solid product. The solid products were combined, and then recrystallized from a solution of $CH_2Cl_2$ and hexanes.

Yield: 6.6 g, 67.4%

Mol. Wt. Calcd. for $C_{33}H_{38}O_4N_2$: 526.2831

High resolution MS: 526.2835

$^1$H NMR in $CDCl_3$: 1.05 (t, 6H) , 1.12 (t, 6H), 2.43 (q, 4H), 2.75 (q, 4H), 3.85 (s, 2H), 5.25 (s, 4H), 7.28–7.40 (m, 10H), 8.70 (br s, 2H).

5,5'-bis(benzyloxycarbonyl)-3,3'-4,4'-tetraethyl-2,2'-dipyrromethane (Compound B of FIG. 2) (8.1 g, 0.015 mole) in 200 ml tetrahydrofuran (THF) was stirred under hydrogen at atmospheric pressure and room temperature overnight in the presence of 0.4 g 10% Pd/C and 5 drops of triethylamine. After the catalyst was filtered through celite, the filtrate was evaporated to dryness on a roto-vap resulting in dicarboxylic acid. The dicarboxylic acid was dissolved in 100 ml N,N-dimethylformamide and heated to boiling under argon for one and one-half hours. The solution was then chilled on ice and an excess of chilled benzoyl chloride (7.2 ml) was added drop-wise to the bis-α-free dipyrromethane (Compound B). The reaction mixture was stirred for 2 hours at 5° C. and the solid product collected by filtration. The solid product was added to 50 ml water and basified using $NaHCO_3$. The solution was heated and held at 60° C. for one hour. The pale yellow product which crystallized from the solutions was filtered and then washed with water.

Yield: 3.4 g, 70.0%

Mol. Wt. Calcd. for $C_{19}H_{26}N_2O_2$: 314.1994

High resolution MS: 314.1994

$^1$H NMR in $CDCl_3$: 1.10 (t, 6H), 1.25 (t, 6H), 2.50 (q,4H), 2.70 (q, 4H), 4.00 (s, 2H), 9.55 (s, 2H), 10.90 (s, 2H).

3,3',4,4'-tetraethyl-5,5'-diformyl-2,2'-dipyrromethane (Compound C of FIG. 2) (1.03 g, 0.0033 mole) in 300 ml ethanol was bubbled with argon for 20 minutes. hydroxylamine hydrochloride (0.51 g, 0.0073 mole) and sodium acetate (1.20 g, 0.015 mole) were added. This mixture was heated at 60° C. under argon for two and one-half hours. The solvent was removed on a roto-vap and the product dried overnight in vacuo. The bis-oxime was dissolved in 5 ml acetic anhydride and saturated with argon for 30 minutes. The crude bisnitrile product (Compound D of FIG. 2) was obtained as a black solid after removal of acetic anhydride and dried under vacuum overnight. The product was purified by silica gel column (40 g) with 0.5% methanol in $CH_2Cl_2$, followed by an alumina column (40 g) with 10–20% EtOAc. Evaporation of the solvent yielded pale pink crystals.

Yield: 0.43 g, 42%

Mol. Wt. Calcd. for $C_{19}H_{24}N_4$: 308.2001

High resolution MS: 308.2002.

$^1$H NMR in $CDCl_3$: 1.10 (t, 6H), 1.25 (t, 6H), 2.45 (q, 4H), 2.60 (q, 4H), 3.90 (s, 2H), 8.45 (s, 2H).

3,3'-4,4'-tetraethyl-5,5'-cyanodipyrromethane (0.053 g, $1.7 \times 10^{-4}$ mole) was dissolved in 10 ml anhydrous THF and added dropwise to a THF suspension of $LiAlH_4$ (0.050 g, $1.5 \times 10^{-3}$ mole) under $N_2$ at 0° C. The resulting mixture was stirred for 30 minutes and two drops of water was added. A solid product formed which was filtered off. The bis-amine product was obtained after evaporation of the solvent by drying under vacuum overnight. The bis-amine was dissolved in 50 ml anhydrous methanol and bis-aldehyde (0.050 g, $1.6 \times 10^{-4}$) was added. The solution was bubbled with $N_2$ for 20 minutes and brought to reflux under $N_2$. Lead thiocyanate ($Pb(SCN_2)$) (0.055 g, $1.7 \times 10^{-4}$ mole) was added and the solution refluxed for 4 hours. Oxygen gas was bubbled through the solution at room temperature overnight. After evaporation of the solvent, the crude porphocyanine product was dried under vacuum overnight. The product was purified by $Al_2O_3$ column (4% water added) with 10% ethyl acetate in $CH_2Cl_2$. The green eluent was collected and concentrated on the roto-vap. Crystals of the porphocyanine macrocycle were obtained after evaporation of the solvent.

Yield: 19.3 mg, 19.1% macrocycle

Mol. Wt. Calcd. $C_{38}H_{48}N_6$: 588.3941

High resolution MS: 588.3933

$^1$H NMR (300 MHz, $CDCl_3$), −4.50 (bs, 2H), 2.05 (t, 12H), 2.13 (t, 12H), 4.28 (q, 8H), 4.40 (q, 8H), 10.50 (s, 2H), 13.0 (s, 4H).

UV/VIS in $CH_2Cl_2$ 455, 592, 800 nm.

EXAMPLE 2

Figure 3:
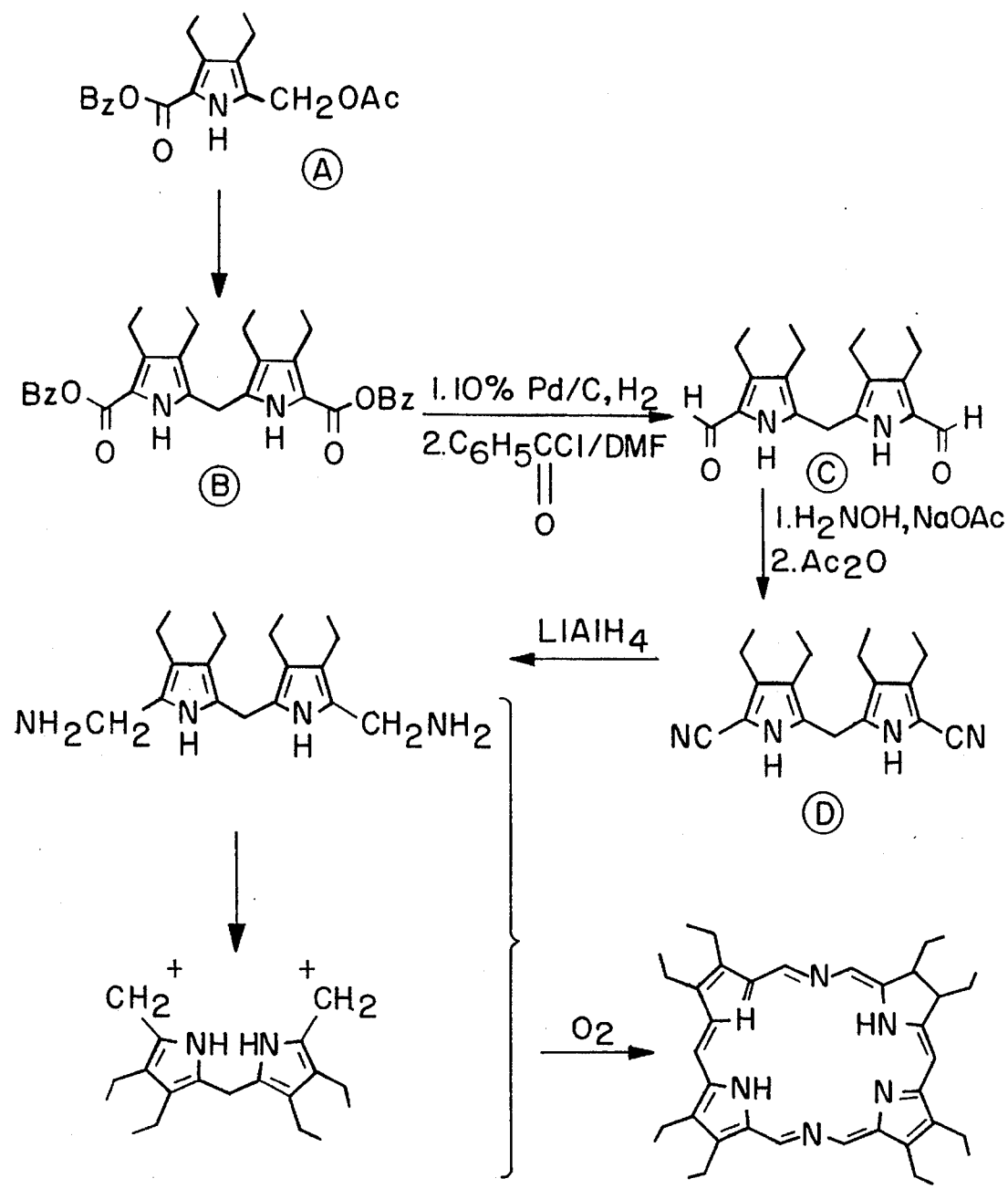
FIG. 3 illustrates another method for synthesizing a porphocyanine of Formula I.

Synthesis of Porphocyanine, FIG. 3

3,3'-4,4'-tetraethyl-5,5'-cyanodipyrromethane was prepared according to the methodology of Example 1. 0.102 g, $3.3 \times 10^{-4}$ mole of 3,3'-4,4'-tetraethyl-5,5'-cyanodipyrromethane in 10 ml anhydrous THF was slowly added to a 20 ml THF suspension of $LiAlH_4$ under $N_2$ at 0° C. The mixture was stirred for 30 minutes and two drops of water were added to quench the reaction. The precipitate was filtered off. The golden colored solution was transferred to a two-neck flask containing equimolar portions of $Pb(SCN)_2$ and anhydrous sodium sulphate. Fifteen milliliters of anhydrous methanol were added and the mixture was brought to reflux. The color of the solution gradually changed from purple to dark green. The reaction was stopped after four and one-half hours and air was bubbled slowly through the solution overnight. The crude product was dissolved in methylene chloride and the solid was filtered off. The volume of the green solution was reduced to approximately 5 ml and then charged on an alumina column (120 g, 4% water added) and eluted with 10% ethyl acetate in $CH_2Cl_2$. Two liters of the bright green eluent containing the porphocyanine was collected and evaporated to dryness.

Yield: 23.4 mg, 24.1%

The spectroscopic data of this compound are identical to the compound prepared in Example 1 above.

EXAMPLE 3

In Vitro Toxicity of Porphocyanine

Cells are washed three times in serum-free medium (DME), counted and made up to a concentration of $10^7$ cells per ml.

For the "affinity" assay, in the dark, 100 µl of the cell suspension and 100 µl of the test or control compound are mixed. "Labeling" is allowed to continue for one hour at 4° C., and labeled cells are washed in the dark three times with 3 ml medium each time and resuspended in fresh medium. The resuspended cells are then subjected to light exposure at 300–850 nanometers for 30 minutes.

In a "direct" assay the cells are irradiated immediately upon addition of the test or control compound. The effect of irradiation is estimated using methods appropriate to the target cells.

When human erythrocytes (RBCs) are used as test cells, the hemolysis caused by irradiation of control (hematoporphyrin, Hp)-labeled and porphocyanine (Formula I)-labeled cells is estimated visually.

When the murine mastocytoma cell line P815 is used, the results are determined as follows:

The cells are labeled as above using concentrations of 10–50 ng/ml of Hp as control and the porphocyanine of Formula I as the test substance. The resuspended cells are treated with 300–850 nm light for 30 minutes and the viability resulting is estimated by direct counting using eosin-Y exclusion, a standard procedure for differentiating living from dead cells.

In other determinations conducted as above, the cells recovered from light exposure are assayed for viability by incubating them for 18 hours in 10 µCi/ml tritium-labeled thymidine according to the standard procedure whereby thymidine incorporation is equated with viability. The cells are harvested and radioactivity uptake is measured by a scintillation counter.

EXAMPLE 4

Selective Binding of Porphocyanine

P815 cells are incubated as described in Example 3 using 1–200 ng/ml Hp or the porphacyanine of Formula I. The cells are labeled in the dark for 30 minutes, washed free of unabsorbed porphyrins, resuspended, and then exposed to 300–850 nm light for another 30 minutes. Viability of the cells is established by tritiated thymidine incorporation after labeling with 30 µCi/ml tritiated thymidine and incubating at 37° C. for 18 hours.

EXAMPLE 5

Preparation of Immunoconjugates

This example describes methods of preparation for immunoconjugates of four different antibody preparations with either hematoporphyrin (Hp) or a porphocyanine (Pc) of Formula I. The antibodies employed are CAMAL-1, anti-M1 antibody, and B16G antibody, all prepared as described hereinabove, and affinity purified rabbit anti-mouse Ig (RαMIg). In addition, a purified irrelevant monoclonal preparation (C-MAb) is used where a control is desired.

One preparation of the conjugates is performed basically as described by Mew et al. (J. Immunol. (1983) 130:1473). Briefly, to 220 mg Hp.0.2 HCl (Sigma Chemical Co., St. Louis, Mo.) in 25 ml water and 0.8 ml N,N-dimethylformamide is added 20 mg 1-ethyl-3-(3-dimethylaminopropyl)-carbodiimide HCl (EDCI) in 0.6 ml water. After 30 minutes, this solution is mixed with 15 mg of the antibody protein dissolved in 5 ml distilled water and incubated for 5 hours. During this period, the pH of the solution is monitored and adjusted to between 6 and 7. Then 50 µl of monoethanolamine is added, and the solution is allowed to stand overnight at room temperature. The solution is dialyzed against 0.001M phosphate buffer pH 7.4 for four days with three changes per day and overnight against PBS. The conjugate of porphocyanine is analogously prepared.

In a preferred protocol, 2 ml of a dispersion in DMSO containing 5 mg each of the Hp or Pc and the dehydrating agent is prepared and stirred for 30 minutes at room temperature under nitrogen. To this is added a dispersion containing 2 mg of the appropriate immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 µl monoethanolamine, and is then dialyzed against PBS using three changed of wash.

Alternatively, 2 ml of a dispersion containing 5 mg each of Hp or Pc, a linking agent, and a dehydrating agent is prepared. and stirred for approximately 15 minutes at room temperature under nitrogen. To this is then added a dispersion containing about 2 mg of the immunospecific protein in 2 ml of tetrahydrofuran and the resulting mixture stirred for another 10 minutes. The mixture is then worked up as described above.

The foregoing procedures are appropriate for CAMAL-1 and for the remaining antibody preparations listed above.

In addition, the following preparations are made specifically with B16G and RαMIg:

B16G

Eleven mg of hematoporphyrin plus 11 mg of EDCI in 4 ml spectral grade DMSO are stirred for 30 minutes under nitrogen at room temperature before the addition of 20 mg lyophilized B16G antibodies, prepared as described by Maier et al. J. Immunol. (1983) 131:1843, in 2 ml DMSO. The resulting mixture is stirred for 40 second at room temperature and working up as described above. The resulting product contains approximately 375 µg Hp/mg B16G. A similar procedure is used substituting Pc for Hp.

RαMIg

Four hundred μg of EDCI and 400 μg hematoporphyrin in 1 ml DMSO are stirred for 30 minutes under nitrogen at room temperature as above before the addition of 800 μg lyophilized RαMIg antibodies, prepared as described by Mew et al. (*J. Immunol.* (1983) 130:1473) in 1 ml DMSO. The resulting mixture is stirred for 30 seconds and worked up as described above to obtain a product containing 200 αg Hp/mg RαMIg. A similar procedure is used substituting Pc for Hp.

EXAMPLE 6

Specificity of Immunoconjugates In Vitro

The Tsm-Hp and Tsm-Pc conjugates wherein the Tsm is comprised of an immunoglobulin are tested against cells in vitro by mixing the conjugates with the appropriate cell types, along with suitable controls, and then exposing the labeled cells to irradiation. Procedures for carrying out this assay are described in detail in Mew et al., *Cancer Research* (1985) for CAMAL-1, and by Mew et al., *J. Immunol.* (1983) for Anti-M1, both references cited hereinabove are incorporated herein by reference.

Briefly, for CAMAL-1, three cell lines, WC4, WC6 and WC2 (WC4 and WC6 produce the CAMAL antigen, but WC2 does not), are labeled with the appropriate Tsm-Hp or Tsm-Pc preparation as described above in Example 4. The labeled cell preparations containing $10^6$ cells each are introduced to Rose chambers and exposed to light activation with a laser at 630 nm. The results for various preparations are then compiled.

For the anti-M1 conjugate, M1 tumor cells are used as target cells and treated with the Tsm-Hp, Tsm-Pc conjugates or drug or antibody alone or the combination of antibody and drug, but uncoupled, by incubating them in a 6% $CO_2$ humidified incubator at 37° C. for two hours. The cells are washed three times in PBS and then plated and exposed to fluorescent light overnight. The cells are assessed for viability by tritiated thymidine uptake as above.

For the B16G conjugates, A10, P815, and L1210 cells are used as target cells. (A10 cells are a T-cell hybridoma which secretes a B16G-reactive T-suppressor factor; P815 cells are also reactive with B16G.) The in vitro study is done using a direct method employing the B16G-Hp or B16G-Pc conjugate or indirectly using unlabeled B16G antibodies and labeled RαMIg-Hp or RαMIg-Pc.

In a direct method, $5\times10^5$ cells are suspended in 1 ml DME/Hepes containing the appropriate Tsm-drug conjugate as test or control at Hp or Pc concentrations of 320, 160, 80, 40 and 20 ng drug/ml. The cells are incubated in the dark at 37° C. for 1 hour, then washed 3 times in 5 ml DME/Hepes, and then resuspended in 1 ml of the same buffer. Three 100 μl test portions of the labeled preparations are dispensed into flat bottom microtiter wells and the remainder of the cell suspensions (700 μl) are exposed to incandescent light (22.5 mW/cm$^2$) at a distance of 20 cm for 1 hour. Then three additional 100 μl aliquots are removed to microtiter wells. Tritium-labeled thymidine diluted in DME/Hepes containing 20% FCS is then added to all microtiter wells in 100 μl aliquots so that 2 μCi of labeled thymidine is added to each well. Cultures are incubated for 18 hours at 37° C. and humidified 10% $CO_2$ and then harvested on a MASH harvester. Thymidine incorporation is measured with an Hp scintillation counter (Tri-Carb Model 4550).

In an indirect assay, the A10 suspended cells, prepared as described above, are exposed to 50 μg/ml of either B16G or a control antibody C-MAb at 4° C. for 30 minutes, washed in DME/Hepes, and then exposed for an additional 30 minutes at 4° C. in the dark to varying concentrations of RαMIg-Hp or RαMIg-Pc between 2 μg/ml and 15 ng/ml of Hp or Pc. The cells are assessed for viability using labeled thymidine uptake as described above.

EXAMPLE 7

In Vivo Cytotoxicity of the Porphocyanine and Conjugates Thereof

The in vivo efficacy of porphocyanine (Pc) and conjugates thereof is also assessed. For the CAMAL-1 and anti-M1 conjugates, the procedures are as described in the two Mew et al. papers referenced above in Example 6. For the B16G-Hp and B16G-Pc conjugates and for the Pc (Formula I) alone, the in vivo studies are conducted as follows:

The in vivo test relies on the indirect effect of a population of T-suppressor cells on tumors, which then serve as means to assess the effectiveness of the irradiation treatment. P815 mastocytoma cells grown in syngeneic DBA/2 mice stimulate T-suppressor cells specific for the tumor. These T-suppressor cells impede the development of specific T-killer cells which would otherwise aid in the regression of the tumor. The T-cell hybridoma designated A10 above secretes a T-suppressor factor which is associated with these T-suppressor cells. Thus, selective killing of these T-suppressor cell populations through reaction with conjugates in which the Tsm is an antibody specific for the T-suppressor factor on the surface of the cells (namely B16G) should result in tumor regression in mice bearing the P815 tumors.

Therefore, in this assay, DBA/2 mice are injected in the right flank subcutaneously with $10^4$ P815 cells to incorporate the tumor. On day eight, when the tumors are palpable (approx. 25–42 sq. mm), the mice are randomly sorted into groups of eight and injected IV with 150 μl PBS containing nothing, Hp or Pc, B16G-Hp or B15G-Pc, B16G plus either drug, B16G alone or C-MAb-Hp or C-MAb-Pc. The levels of Hp are 50 μg per animal in all cases and B16G 310 μg in all cases (where appropriate).

The animals are maintained in the dark for two hours and then exposed to strong light at 300–850 nm and 22.5 mW/cm$^2$. The animals are then treated normally and monitored on a daily basis.

EXAMPLE 8

Diagnostic Imaging

A 32-year old female patient develops fever and abdominal pain. The patient is maintained on antibiotic therapy for a period of one week without effect. A CAT scan fails to demonstrate any abnormal mass. Radioimaging studies are performed using Tc-99m-labeled porphocyanine. An injection of 20 mCi of the radiolabeled porphocyanine is used and the patient is scanned with a gamma camera in SPECT mode. The scan of the patient's abdomen demonstrates a focus of accumulation of Tc-99m. Surgery is performed and an abscess is found at the site of the Tc-99m activity.

EXAMPLE 9

Figure 11:
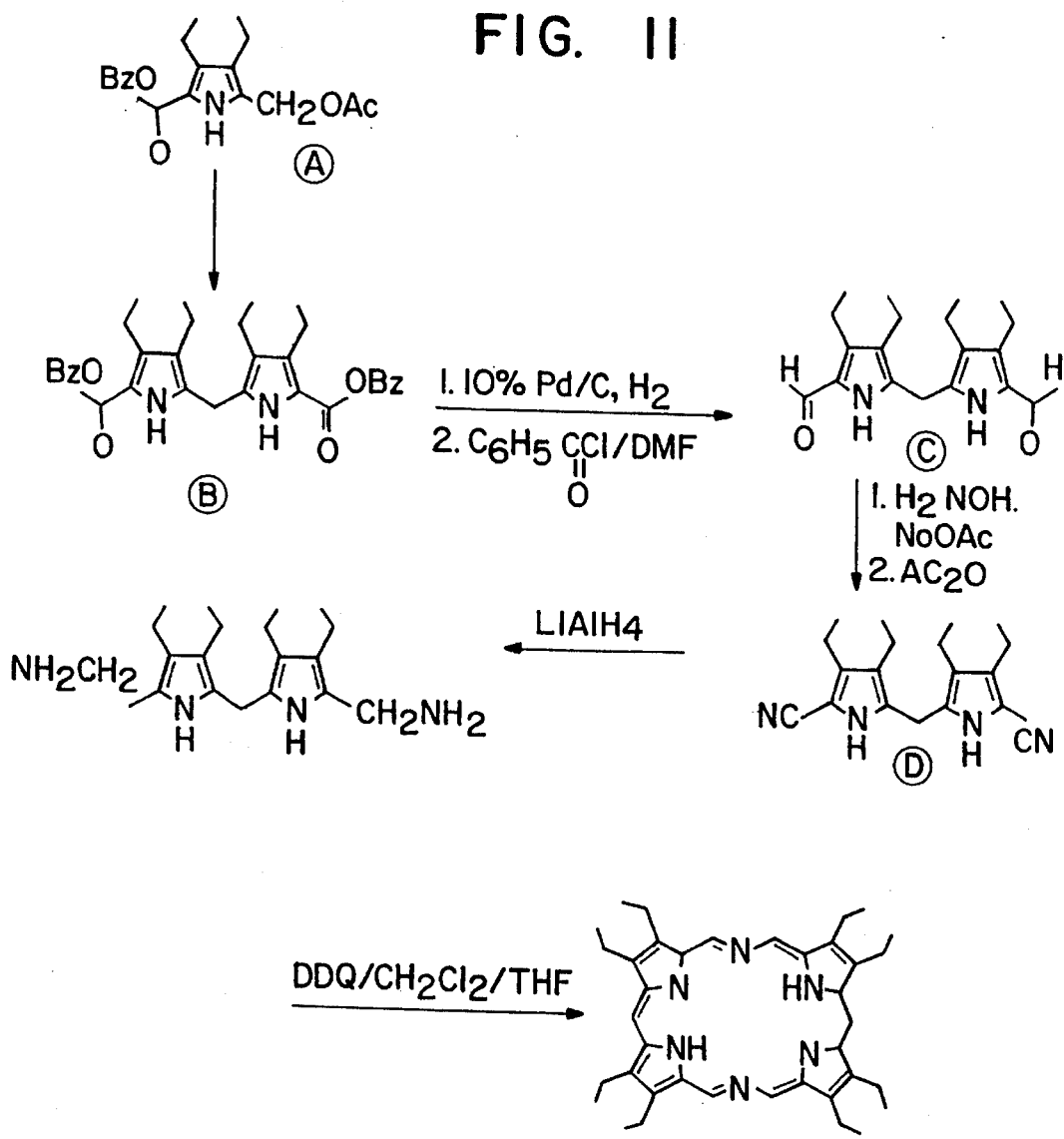
FIG. 11 illustrates a novel method for synthesizing a porphocyanine of Formula I.

Synthesis of Porphocyanine, FIG. 11

3,3'-4,4'-tetraethyl-5,5'-cyanodipyrromethane was prepared according to the methodology of Example 1. A tenfold excess of 2,3-dichloro-5,6-dicyano-1,4-benzoquinone (DDQ) was added to 69 mg of 3,3'-4,4'-tetraethyl-5,5'-cyanodipyrromethane in 10 ml anhydrous THF. The resulting solution turned dark green immediately. The residue was chromatographed according to the methodology of Example 2. A significant increase in yield was obtained when compared to air oxidation.

Yield: 32 mg, 48%

The spectroscopic data of this compound are identical to the compound prepared in Example 1 above.

EXAMPLE 10

Synthesis of Porphocyanine, Simplified Method

In an alternative method for synthesizing porphocyanine, the dialdehyde was prepared according to the methodology of Example 1. 25 mg of 3,3'-4,4'-tetraethyl-5,5'-diformyl-2,2'-dipyrromethane was suspended in 30 ml dry EtOH. The resulting ethanol solution was chilled at 0° C. and ammonia gas was bubbled through it for 30 minutes. The gas inlet was then removed and the flask placed in an oil bath at 60° C. for 72 hours. The reaction was stopped and cooled at 0° C. Ethanol was removed on the roto-vap and the residue was chromatographed on neutral Alumina (4% H$_2$O added) with dichloromethane.

Yield: 4.6 mg, 20%

The spectroscopic data of this compound are identical to the compound prepared in Example 1 above. Another 1.5 mg of product was obtained from the oxidation of the more polar component by DDQ.

We claim:

1. A method for synthesizing a porphocyanine having the formula:

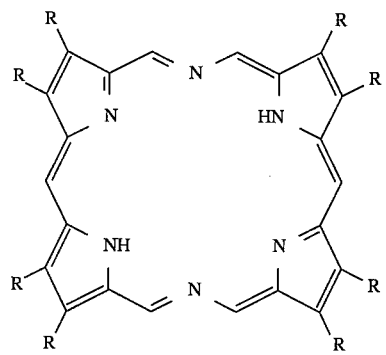

wherein each R is a ethyl, comprising the steps of:
  (a) adding a ten-fold excess of 2,3-dichloro-5,6-dicyano-1,4-benzoquinone to 3,3'-4,4'-tetraethyl-5,5'-bisaminomethyl-2,2'-dipyrromethane to produce a crude product;
  (b) purifying the crude product by chromatography on an alumina column; and then
  (c) evaporating the purified porphocyanine to dryness.

2. A method for synthesizing a porphocyanine having the formula:

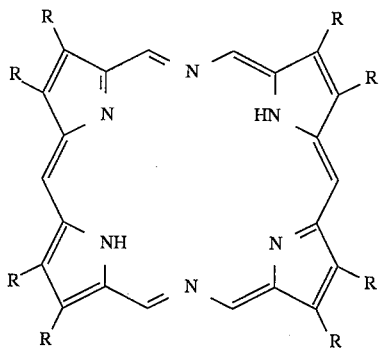

wherein each R is ethyl, comprising the steps of:
  (a) suspending 3,3'-4,4'-tetraethyl-5,5'-diformyl-2,2'-dipyrromethane in dry ethanol;
  (b) bubbling ammonia gas through the solution of step (a);
  (c) heating the product of step (b) at least about 60° C. for at least about 72 hours;
  (d) cooling the product of step (c) to 0° C.;
  (e) purifying the crude product by chromatography on an alumina column; and then
  (f) evaporating the purified porphocyanine to dryness.

* * * * *